United States Patent
Eshuis et al.

(10) Patent No.: US 10,478,140 B2
(45) Date of Patent: Nov. 19, 2019

(54) NEAREST AVAILABLE ROADMAP SELECTION

(71) Applicant: KONINKLIJKE PHILIPS N.V., Eindhoven (NL)

(72) Inventors: Pieter Gerben Eshuis, Best (NL); Peter Maria Johannes Rongen, Eindhoven (NL); Fransciscus Joannes Leonardus Everaerts, Weert (NL); Bram Antonius Philomena Van Rens, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 223 days.

(21) Appl. No.: 14/901,534

(22) PCT Filed: Jun. 27, 2014

(86) PCT No.: PCT/EP2014/063672
§ 371 (c)(1),
(2) Date: Dec. 28, 2015

(87) PCT Pub. No.: WO2014/207188
PCT Pub. Date: Dec. 31, 2014

(65) Prior Publication Data
US 2016/0135770 A1 May 19, 2016

(30) Foreign Application Priority Data
Jun. 28, 2013 (EP) .................................. 13174351

(51) Int. Cl.
*A61B 6/00* (2006.01)
*A61B 6/04* (2006.01)

(52) U.S. Cl.
CPC ............ *A61B 6/485* (2013.01); *A61B 6/0407* (2013.01); *A61B 6/4417* (2013.01);
(Continued)

(58) Field of Classification Search
CPC .................................. A61B 6/485; A61B 6/00
See application file for complete search history.

(56) References Cited

U.S. PATENT DOCUMENTS 5,077,769 A * 12/1991 Franciose .............. A61B 6/481
348/E5.089
7,298,824 B2 11/2007 Watanabe
(Continued)

FOREIGN PATENT DOCUMENTS

EP 1220156 A2 3/2002
EP 1248235 A2 9/2002
(Continued)

OTHER PUBLICATIONS

J. Bredno et al., "Algorithmic Solutions for Live Device-to-Vessel Match". In Proceedings of SPIE—vol. 5370—Medical Imaging 2004: Image Processing, J. Michael Fitzpatrick, Milan Sonka, Editors, May 2004, pp. 1486-1497.

*Primary Examiner* — Joel F Brutus

(57) ABSTRACT

A system and method for vascular roadmapping include an X-ray imaging device for generating a fluoroscopy image, a data base in which a plurality of contrast-enhanced images is stored, a user interface element and a processor. Each of the contrast-enhanced images is stored together with the imaging parameters based on which the image is generated. The user interface element may be configured for selecting any intended imaging parameters, such as by manually adjusting the imaging device in any position and orientation. The processor may be configured for identifying a stored contrast-enhanced image out of the plurality of contrast-enhanced images, which is generated with specific imaging parameters, where the deviation of the specific imaging parameters from the intended imaging parameters is as small
(Continued)

as possible, thus the processor may be configured for identifying the nearest available roadmap.

14 Claims, 6 Drawing Sheets

(52) U.S. Cl.
CPC ............ *A61B 6/4441* (2013.01); *A61B 6/463* (2013.01); *A61B 6/467* (2013.01); *A61B 6/481* (2013.01); *A61B 6/487* (2013.01); *A61B 6/503* (2013.01); *A61B 6/504* (2013.01); *A61B 6/5205* (2013.01); *A61B 6/5235* (2013.01); *A61B 6/545* (2013.01); *A61B 6/547* (2013.01); *A61B 6/5288* (2013.01)

(56) References Cited

U.S. PATENT DOCUMENTS

| | | | |
|---|---|---|---|
| 7,454,043 | B2 | 11/2008 | Eck et al. |
| 7,609,814 | B2 | 10/2009 | Baumgart |
| 7,826,884 | B2 | 11/2010 | Baumgart |
| 8,255,037 | B2 | 8/2012 | Florent et al. |
| 2002/0045817 | A1 | 4/2002 | Ichihashi |
| 2004/0034329 | A1 | 2/2004 | Mankus et al. |
| 2005/0251028 | A1 | 11/2005 | Boese |
| 2006/0120581 | A1* | 6/2006 | Eck .................. A61B 6/481 382/128 |
| 2006/0195475 | A1 | 8/2006 | Logan et al. |
| 2006/0215817 | A1 | 9/2006 | Watanabe |
| 2007/0274449 | A1 | 11/2007 | Camus |
| 2008/0027316 | A1 | 1/2008 | Baumgart |
| 2008/0125649 | A1* | 5/2008 | Meyer ............... A61B 6/0457 600/426 |
| 2009/0180591 | A1 | 7/2009 | Baumgart |
| 2009/0192385 | A1* | 7/2009 | Meissner ........... A61B 6/032 600/426 |
| 2010/0004903 | A1 | 1/2010 | Fargas et al. |
| 2010/0049038 | A1 | 2/2010 | Florent et al. |
| 2010/0057722 | A1 | 3/2010 | Nakamura et al. |
| 2012/0030575 | A1 | 2/2012 | Cok |

FOREIGN PATENT DOCUMENTS

| | | |
|---|---|---|
| JP | 2010240156 A | 10/2010 |
| WO | 0203863 A1 | 1/2002 |
| WO | 2009019640 A2 | 2/2009 |
| WO | 20110021907 A3 | 2/2011 |
| WO | 2011042834 A1 | 4/2011 |

* cited by examiner

NEAREST AVAILABLE ROADMAP SELECTION

CROSS-REFERENCE TO PRIOR APPLICATIONS

This application is the U.S. National Phase application under 35 U.S.C. § 371 of International Application No. PCT/EP2014/063672, filed on Jun. 27, 2014, which claims the benefit of European Patent Application No. 13174351.0, filed on Jun. 28, 2013. These applications are hereby incorporated by reference herein.

FIELD OF THE INVENTION

The present invention relates to method of and system for vascular roadmapping. Especially, the invention relates to a method of and system for selecting a nearest available cardiac roadmap. Furthermore, the invention relates to a computer program for executing the method.

BACKGROUND OF THE INVENTION

After for example a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms.

During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled.

An overlay technique of the angiogram into the live images (referred to as roadmapping) may be utilized. In such procedures, the vessel structure itself is not visible during the intervention as it is not radio-opaque. Consequently, the navigation and precise positioning of guidewire and interventional devices is tedious, time-consuming, and requires additional contrast agent bursts to clarify the position of the devices relative to the relevant vessels. Due to scatter, both patient and medical staff are exposed to x-ray during the acquisition of diagnostic angiograms and interventional fluoroscopy. Navigation support is desired to reduce the intervention time and to enhance the positioning accuracy. Routinely, a static diagnostic angiogram acquired with similar imager geometry is displayed next to the live interventional fluoroscopy. For the navigation of guidewire and devices within the vessels, a subjective visual fusion of the static angiogram and the live fluoroscopy is required. An improved context-rich visualization could give important support in navigation. As an approach, preprocessed angiograms can be overlaid onto the fluoroscopic image stream so that vessels and the interventional devices are synchronously displayed on one screen.

A navigation system can therefore help the cardiologists by providing a cardiac roadmap displayed next or overlaid on the live fluoroscopy pictures. Ideally, this cardiac roadmap represents the vessel network acquired during angiography, with the same cardiac phase than the current live image, and registered with respect to breathing movements and patient motions.

In WO 2004034329 A2, there is described a basic method for realizing cardiac roadmapping, relying on the extraction of the cardiac and respiratory cycles, and on the matching of those cycles between the angiogram images (in filled state) and the live images.

Roadmapping is a very important feature since it provides (hopefully) the accurate localization of the intervention device with respect to the vessel anatomy (otherwise invisible during most of the PCI (Percutaneous Coronary Intervention) time).

Roadmapping is even more interesting in the case of cardiac interventions since the mental registration otherwise performed by the cardiologist between the angiogram (usually one selected image) and the dynamic fluoroscopy sequence is a tiring and inaccurate process.

U.S. Pat. No. 5,077,769 describes a control panel, which includes a programmable electroluminescent touch screen and a joystick, which is mounted so as to be operable by the radiologist during a PTCA procedure. A bedside monitor displays fluoro and roadmap information during the procedure. The radiologist can adjust the relative weight of the roadmap information to the fluoro information by operating the joystick. The system automatically selects the appropriate roadmap based upon the angular orientation of the camera gantry, or alternatively selects the appropriate gantry position to correspond to that used to produce a satisfactory roadmap.

However, the enhanced fluoroscopy sequence that contains the roadmapping mask that comes from the angiogram sequence suffers from several serious drawbacks.

It is quite impossible to overlay the full angiogram to the fluoroscopy image because this creates background mixings and all sorts of disagreeable visual effects.

Other drawbacks are related to fluoroscopy. The navigation image (a real-time fluoroscopy sequence) is very noisy, and it contains possibly strong breathing motion.

SUMMARY OF THE INVENTION

Dynamic 2D Cardiac roadmapping requires the availability of roadmaps, created and calculated from exposure images during injection of a contrast agent into the coronary arteries. Ease-of-use may be a main feature of the application. One particular problem at hand, while navigating with the guide wire, the C-arc and the patient table may be seen as: Which roadmap, of the ones available, is most suitable for use at the current position?

Moreover, interventional cardiologists are under production pressure, meaning they want to treat the patient in the shortest possible time. So there is no time to inspect a list of available runs by hand.

In fact, the requirement is to have an automated answer/action to the question above.

The present invention proposes to automatically adapt imaging parameters of an imaging device for a fluoroscopy image to imaging parameters of an already generated contrast-enhanced image. It is an object of the invention to provide a method and device eliminating or at least reducing the above mentioned drawbacks.

This is achieved by the subject matter of each of the respective independent claims. Further embodiments are described in the respective dependent claims.

In general, a system for vascular roadmapping in accordance with the invention comprises an X-ray imaging device for generating a fluoroscopy image, a data base in which a plurality of contrast-enhanced images is stored, a user interface element and a processing device. Each of the contrast-enhanced images is stored together with the imaging parameters based on which the image is generated. The user interface element may be configured for selecting any intended imaging parameters, for example by manually adjusting the imaging device in any position and orientation.

The processing device may be configured for determining current imaging parameters of the imaging device. The processing device may further be configured for identifying a stored contrast-enhanced image out of the plurality of contrast-enhanced images, which is generated with specific imaging parameters, wherein the deviation of the specific imaging parameters from the intended imaging parameters is as small as possible, thus the processing device may further be configured for identifying the nearest available roadmap. The processing device may further be configured for automatically controlling the imaging device so as to adjust the imaging parameters of the imaging device to the specific imaging parameters of the identified contrast-enhanced image.

The imaging parameters may comprise a position of the x-ray source and the x-ray detector, an orientation of the x-ray source and the x-ray detector, settings of the x-ray source, and settings of the x-ray detector, a position of a patient table, field-of-view, frame speed, left/right coronary artery, time and date of generation of a contrast-enhanced image, and smallest possible foreshortening.

According to an embodiment, the processing device of the system may be further configured for determining a ready-for-use-state of the imaging device. That is, the processing device monitors for example an adjusting action of the imaging device and provides a feedback as soon as the adjusting action is completed. The user interface element may be configured to indicate the state of the imaging device as provided by the processing device.

According to another embodiment, the processing device may be further configured for generating a roadmap scatterplot including available contrast-enhanced images with imaging parameters being close to the intended imaging parameters. The user interface element may provide the possibility to skip through the available contrast-enhanced images, i.e. roadmaps, and/or to select one out of the plurality of available roadmaps.

The processing device of the system may further be adapted to detect at least a portion of an instrument in the fluoroscopy image. The processing device may thus be capable of automatically determine an anatomical region of interest in a fluoroscopy image.

It is noted that the instrument might be, on the one hand, a flexible or stiff catheter or wire tip or an electrode, and on the other hand also a biopsy device, a cannula or trocar. It can also be an endoprothesis such as a stent, an occluder (e.g. a Patent Foramen Oval occluder), an artificial valve, etc. . . .

Furthermore, the processing device may be adapted to combine a fluoroscopy image with a contrast-enhanced image and to display the combined image on a monitor, for example as an overlay of the contrast-enhanced image on the fluoroscopy image.

According to another embodiment, the processing device of the system is adapted to identify a cyclic motion in a series of contrast-enhanced images and is adapted to identify a cyclic motion in a series of fluoroscopy images, wherein the processing device is further adapted to combine a selected fluoroscopy image with a contrast-enhanced image of a corresponding motion cycle. This can be achieved by a purely image-based method, or through the use of external non-imaging systems such as ECG (electro cardiogram) signal.

According to another aspect, a method for vascular roadmapping comprises the steps of receiving intended imaging parameters for a fluoroscopy image, determining a contrast-enhanced image generated with specific imaging parameters, wherein the deviation of the specific imaging parameters from the intended imaging parameters is as small as possible, and automatically controlling an imaging device so as to adjust the imaging parameters of the imaging device to the specific imaging parameters.

Because the images used for navigation purposes, may now be contrast-enhanced images like angiograms or atriograms or ventriculograms, the image quality at navigation time becomes that of contrast-enhanced imaging time, that may be much better than the fluoroscopy image quality.

Because only the best filled e.g. angiogram cardiac cycle may be selected for this process, the breathing motion may be now reduced to a single cardiac cycle. If breath-hold (even relative) is requested from the patient, the breathing motion during about 1 second (=1 cardiac cycle) may virtually be reduced to zero.

The method may further comprise the steps of generating a fluoroscopy image with the specific imaging parameters, wherein the image may include an instrument in the anatomy part, receiving from a data base the contrast-enhanced image with the same specific imaging parameters, and combining the fluoroscopy image with the contrast-enhanced image.

According to an embodiment, the method further comprises the step of providing a ready-for-use-state of the imaging device.

According to another embodiment, the method further comprises the step of providing a roadmap scatterplot including available contrast-enhanced images with imaging parameters being close to the intended imaging parameters.

The method may further comprise the step of displaying the combined images.

Therefore, instead of navigating within the fluoroscopy world, the navigation could occur within the angiogram world, virtually free of noise and of breathing motion, and with an optimal view of the vessels, possibly with an additional overlay of an intervention device.

It is noted that a portion of interest of an instrument may be detected in a fluoroscopy image manually or by means of automatic procedures utilizing appropriate image processing computer software.

The result of the method, i.e. the achieved combined images, may be displayed on a suitable device, for example on a monitor.

The method according to the invention may be used advantageously by an imaging system for PCI (Percutaneous Coronary Intervention) in catheter laboratories, to treat cardiac stenoses.

According to a further aspect of the invention, a computer program for vascular roadmapping is provided which, when executed on a processing device of the system according to the invention, causing the system to perform the method according to invention. Therefore, the method according to the invention may be performed substantially automatically, or at least predominantly automatically. Therefore, the computer program may comprise sets of instructions for gathering and at least temporarily storing at least one contrast-enhanced image generated by an appropriate system, wherein the imaging parameters based on which this contrast-enhanced image has been generated are nearest relative to intended imaging parameters. The computer program may further comprise sets of instructions to adjust an imaging device to the imaging parameters of the contrast-enhanced image, and sets of instructions for gathering and at least temporarily storing at least one live fluoroscopy image generated by an appropriate system based on the imaging parameter of the contrast-enhanced image.

Such a computer program is preferably loaded into a work memory of a data processor. The data processor is thus equipped to carry out the method of the invention. Further, the invention relates to a computer readable medium, such as a CD-ROM, at which the computer program may be stored. However, the computer program may also be presented over a network like the World Wide Web and can be downloaded into the work memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of the embodiments to be described herein after and are explained with reference to examples of embodiments also shown in the figures, but to which the invention is not limited.

DETAILED DESCRIPTION OF EMBODIMENTS

In the following, a quick and easy way is described to meet the requirements above. An automated means for finding the so-called nearest available roadmap is provided, both in space and time. A roadmap may be automatically selected and activated, offering a physician the possibility to automatically go to the proposed position by means of automatic position control.

Figure 1:
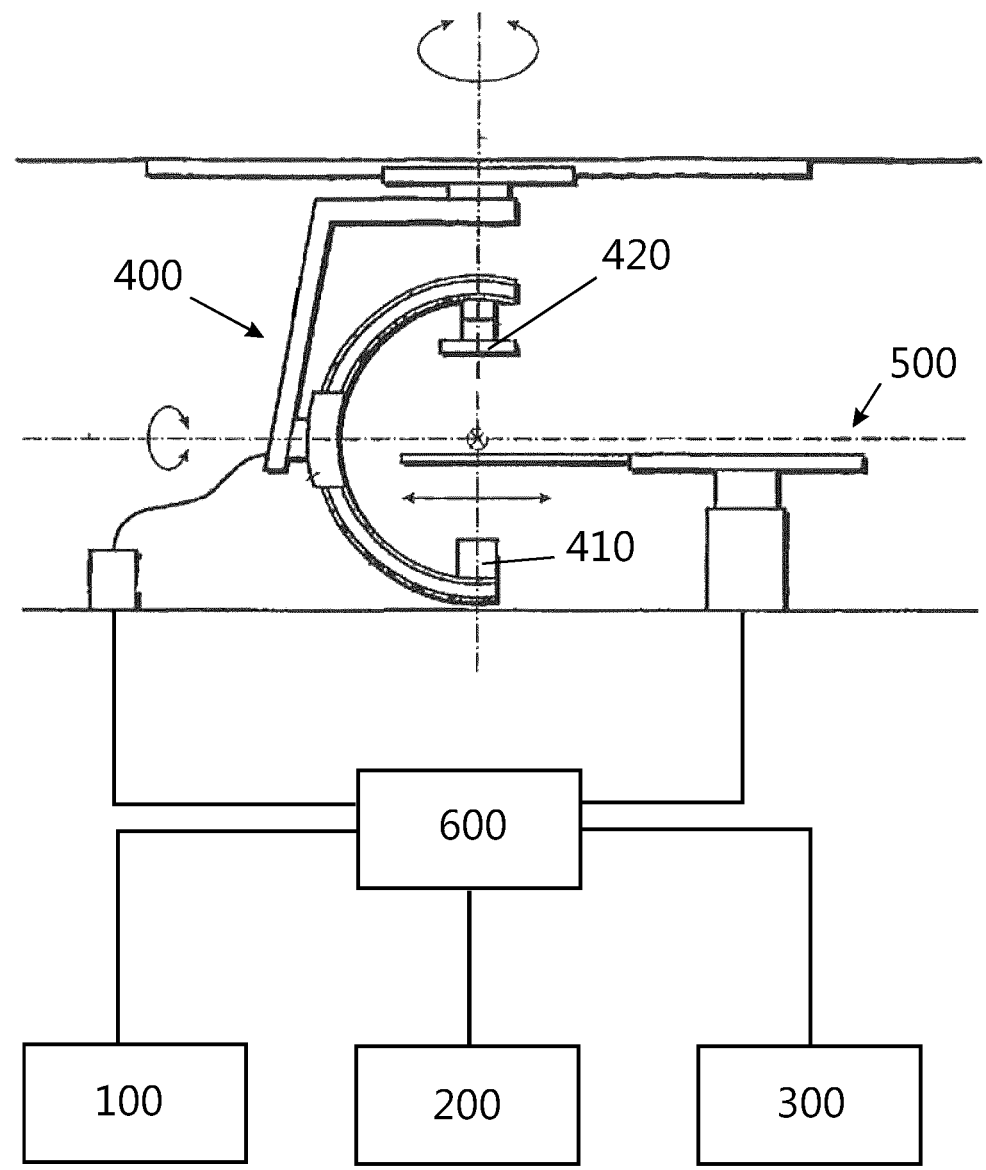
FIG. 1 shows a system for vascular roadmapping according to an embodiment.

FIG. 1 shows an exemplary system according to the invention, the system including a processing device 600 which is connected on the one hand with an imaging system 400 as well as a patient table 500, and on the other hand with a data base 100, a user interface element 200 and a monitor 300.

The imaging system 400 may be an x-ray system arranged relative to a patient positioned on the table 500, such that a fluoroscopy image of a region of interest may be generated. The processing device 600 may control the generating of the fluoroscopy image by means of the imaging system 400. The imaging system 400 may include an x-ray source 410 as well as a detector for x-ray radiation 420, wherein both, the x-ray source 410 as well as the x-ray detector 420 may be arranged at a C-arm to ensure a proper orientation of both, relative to each other.

The data base 100 may provide a plurality of contrast enhanced images. Each of those images may be generated previously and may be stored together with the imaging parameters defining as to how the respective image has been generated. The data base may be physically located as part of the processing device 600 in the system, but may also be located for example in a network.

The user interface element 200 may be an interactive operating element, providing possibilities to input commands, but also providing information regarding the state of the system. Examples of user interface elements are described below.

The system further includes a monitor 300 for an illustration of images generated in accordance with a described embodiment. It will be understood, that also information concerning available roadmaps or information concerning the current position and orientation as well as the state of each part of the system may be shown on the monitor.

In the processing device 600, a unit may be provided, for example a working memory on which a computer program for performing the vascular roadmapping, may be stored and/or executed.

Figure 2:
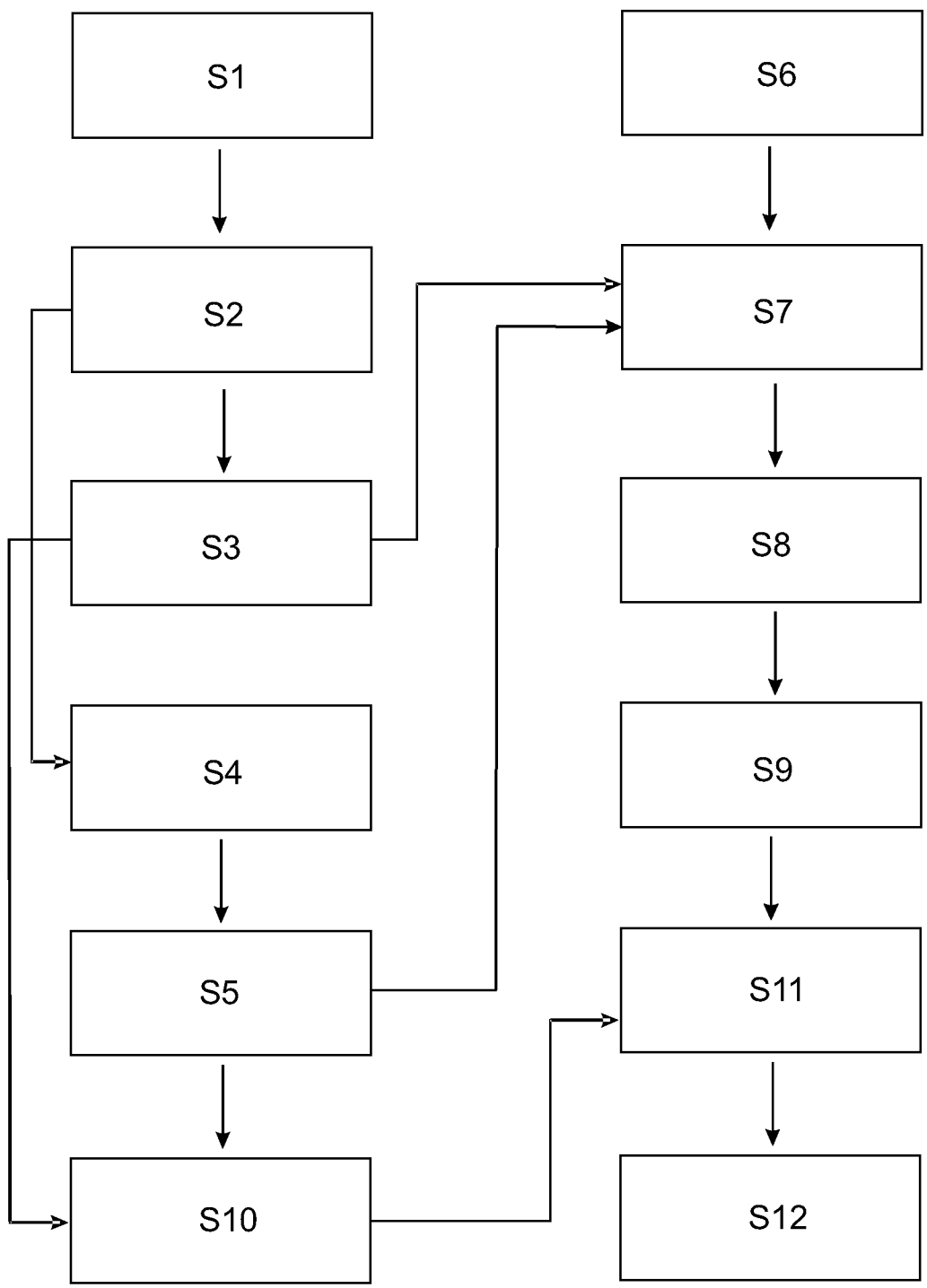
FIG. 2 shows flowchart of a method according to an embodiment.

The flowchart in FIG. 2 illustrates the principle of such vascular roadmapping, comprising the following steps. It will be understood that the steps described with respect to the method are major steps, wherein these major steps might be differentiated or divided into several sub steps. Furthermore, there might be also sub steps between these major steps. Therefore, a sub step is only mentioned if that step is important for the understanding of the principles of the method according to the invention.

In step S1, the system may receive an input representing intended imaging parameters. For example, the imaging system may be adjusted to any position and orientation suitable to generated images of a region of interest of a patient. Such adjusting may be performed at a control unit of the imaging system, wherein the control unit may be integrated in the user interface element. Otherwise, parameters like an imaging direction may be input directly.

In step S2, the nearest available roadmap is determined. That is, the imaging parameters of the contrast-enhanced images stored in the data base are compared with the intended imaging parameters, and the imaging parameters with the smallest deviation from the intended imaging parameters are identified as the nearest imaging parameters.

In step S3, the contrast-enhanced image generated with the nearest imaging parameters is automatically selected.

Alternatively, also a plurality of available roadmaps may be determined in step S2, including roadmaps the imaging parameters of which can be considered as being near to the intended imaging parameters. In step S4, a scatterplot may be generated illustrating one or more of the available roadmaps with the respective imaging parameters in relation to the intended imaging parameters.

Based on the roadmap scatterplot of step S4, one of the contrast-enhanced images may be manually selected in step S5.

In step S6, the current imaging parameters are determined.

Starting from the current imaging parameters determined in step S6, the imaging parameters of the imaging system are adjusted to the imaging parameters of the selected contrast-enhanced image, in step S7. If the adjustment is complete, a ready-for-use-state may be indicated in step S8. As long as the adjustment is not yet completed, a not-ready-for-use-state may be indicated, for example on the user interface element and/or on the monitor of the system.

In step S9, at least one fluoroscopy image is generated. In case, a series of live fluoroscopy images is generated, step S9 may also include the using of ECG signals and/or image processing techniques to determine to which of the selected contrast-enhanced images the current fluoroscopy image having the same cardiac cycle, i.e. to which it corresponds, and through which it geometrically transforms (typically a translation suffices to compensate for breathing motion). The output of this step may be the angiography frame index, and the matching geometrical transform parameters. The angiography frame that corresponds best to the current fluoroscopy image (same cardiac cycle), may simply be selected from the extracted motion cycle in the angiography images.

In step S10, the contrast-enhanced image is received from the data base, with the imaging parameters as automatically (in step S3) or manually (in step S5) selected.

In step S11, both images, i.e. the new fluoroscopy image and the previously generated and stored contrast-enhanced image, may be combined. The images may be simply registered through the application of geometrical transform parameters.

In step S12, the result is displayed for example on a monitor.

Figure 3:
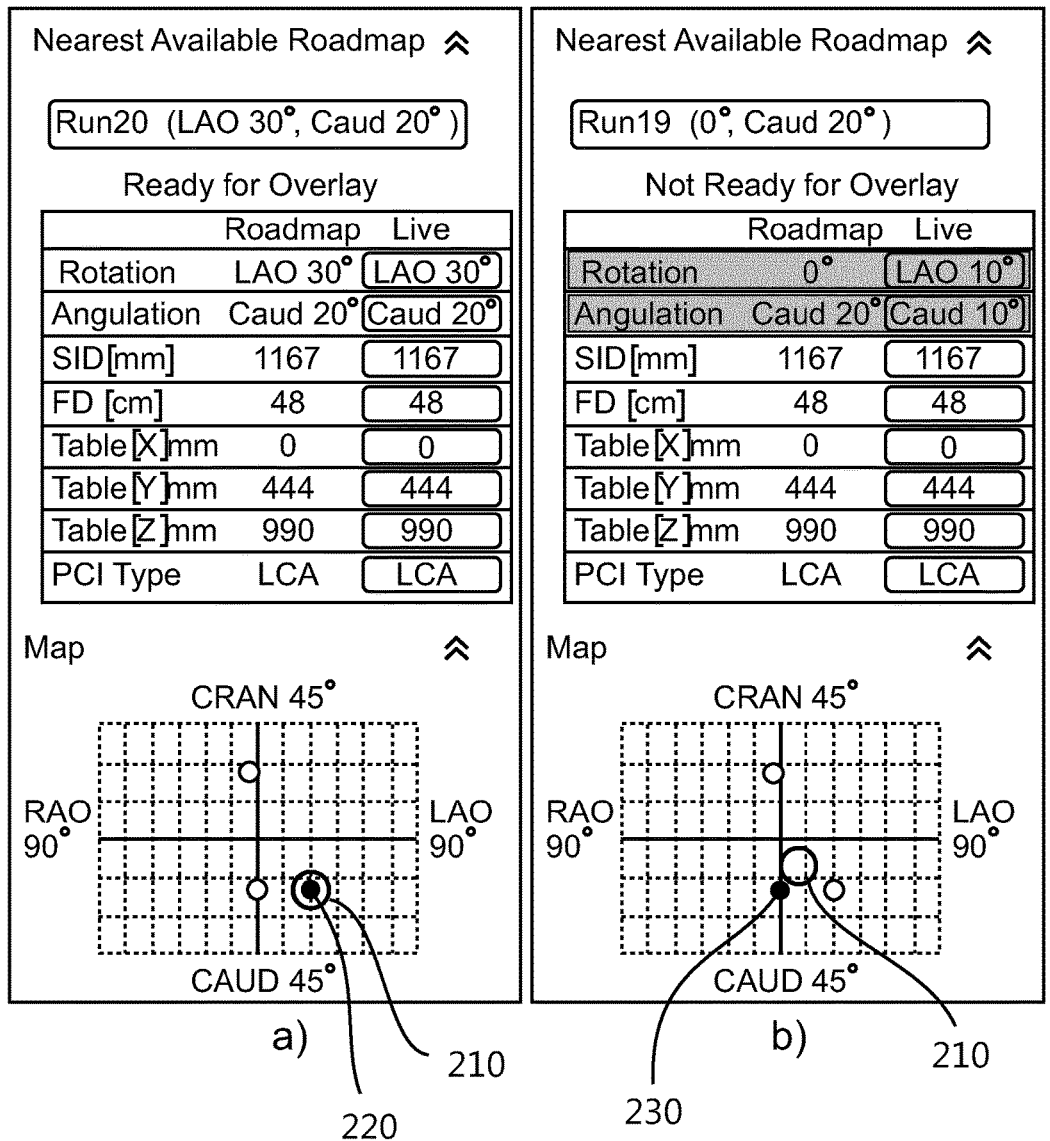
FIG. 3 shows an example of visualization of imaging parameters for available roadmaps.

FIG. 3 illustrates two examples of visualizations which may provide information on the state of an imaging system to a physician. Situation (a) is in the state "ready for overlay": the live conditions (indicated by reference number 210) match the currently selected roadmap conditions (indicated by reference number 220). The selected roadmap may be shown in green. Situation (b) is in the state "not ready for overlay": the system has moved to another position. The application, however, automatically selected the most nearby roadmap: for example a red bullet may indicate the selected roadmap (indicated by reference number 230) which is the closest one to the circle 210 (the actual position of the system). In the two grey lines, it can be seen that the parameters of the rotation and the angulation of the nearest roadmap differ from the respective parameters of the imaging system (Live).

It is noted the "most nearby" has both a spatial and temporal meaning, i.e. the last roadmap created at the closest geometric position.

Figure 4:
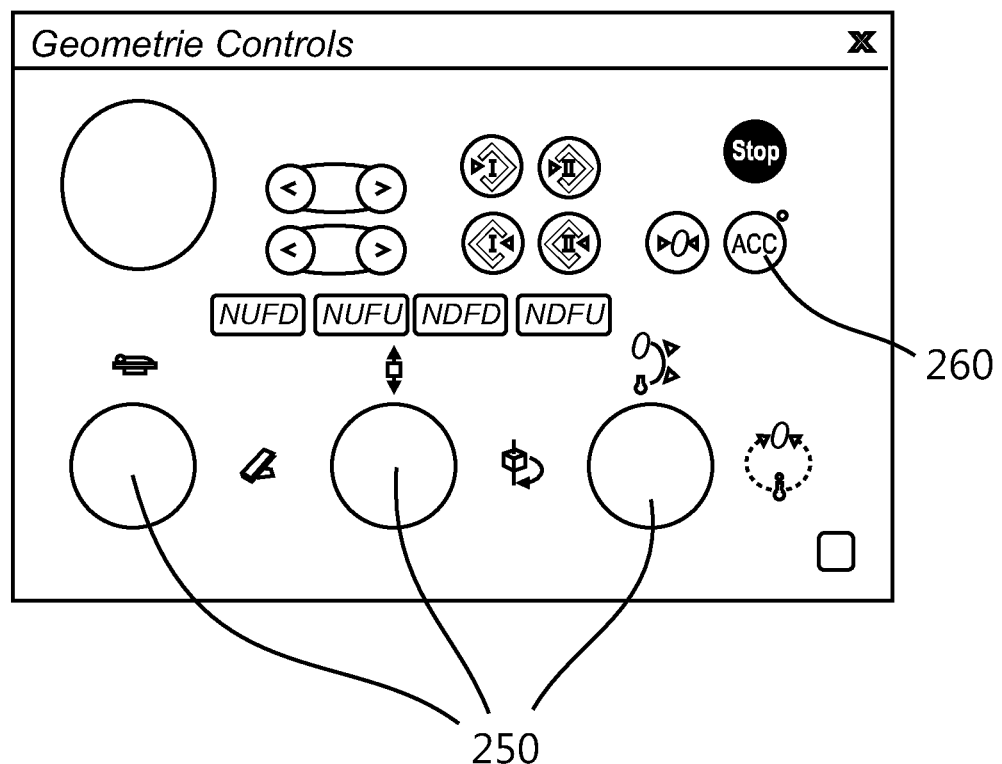
FIG. 4 shows an example of visualization of an input mask for adjusting an imaging device.

Upon activation of the nearest roadmap, the automatic position control becomes active, as shown in FIG. 4. The physician can then easily navigate the C-arc to the proposed position, for example by using the buttons 250. An alternative possibility is by automatic roadmap selection. If the physician moves the C-arc to a position for which a roadmap is readily available the system automatically selects this roadmap (of course, since this is the closest roadmap), makes it active and the system jumps to the "Roadmap Ready" state. Furthermore, a button 260 may be provided. Pressing (and holding) the button 260 will automatically move the imaging system to the proposed, i.e. nearest position (with the specific imaging parameters).

Figure 5:
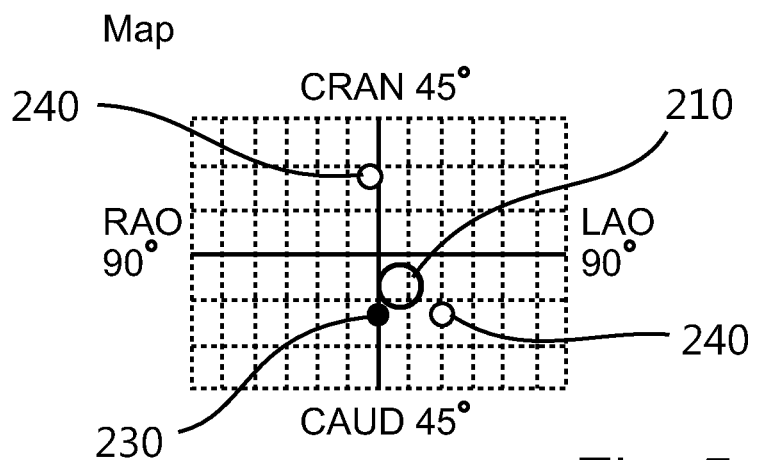
FIG. 5 shows an exemplary visualization of a roadmap scatterplot.

FIG. 5 shows an example of a roadmap scatterplot including three available roadmaps 230, 240, with the nearest roadmap 230 being for example colored. The application shows this selection process in such a "smart map" (scatter plot), showing all available roadmaps 230, 240, the currently selected one with an indication if the system is "ready for roadmap" (green or red), and the current position 210 of the system (for example an orange circle).

Figure 6:
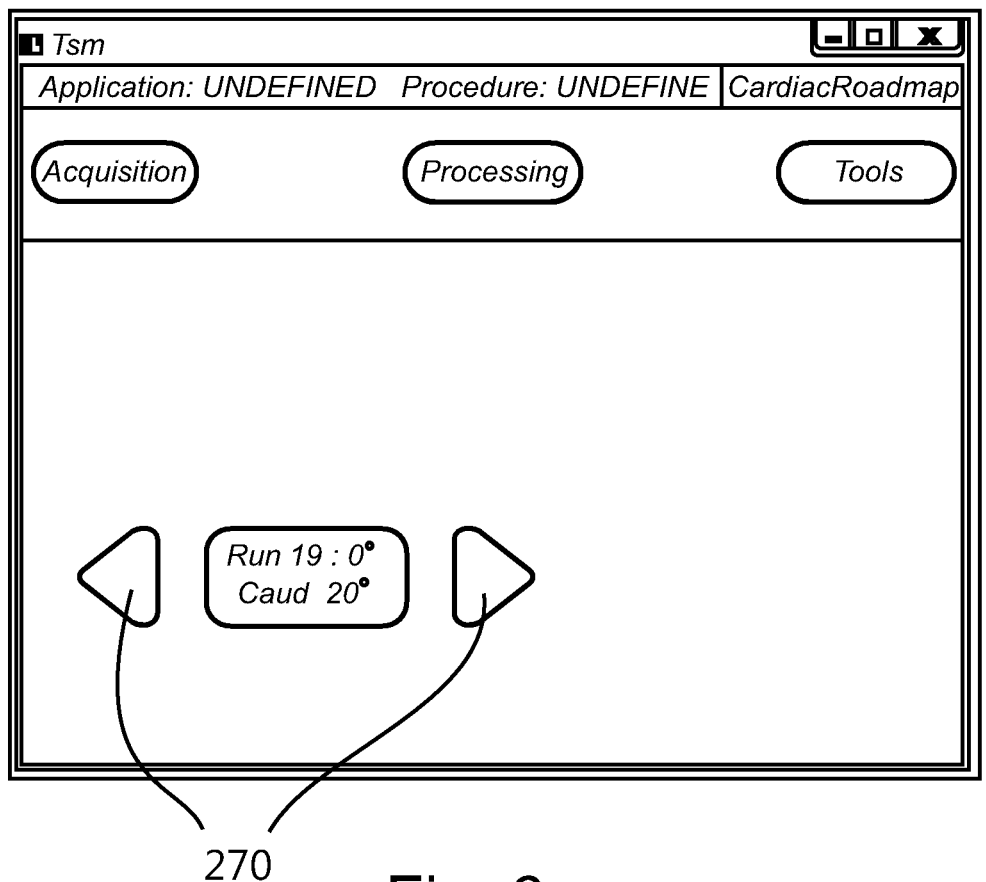
FIG. 6 shows an example of visualization of an input mask for selecting an available roadmap.

As shown in the example in FIG. 6, buttons 270 may be provided that support easy roadmap selection through a list of available roadmaps.

Figure 7:
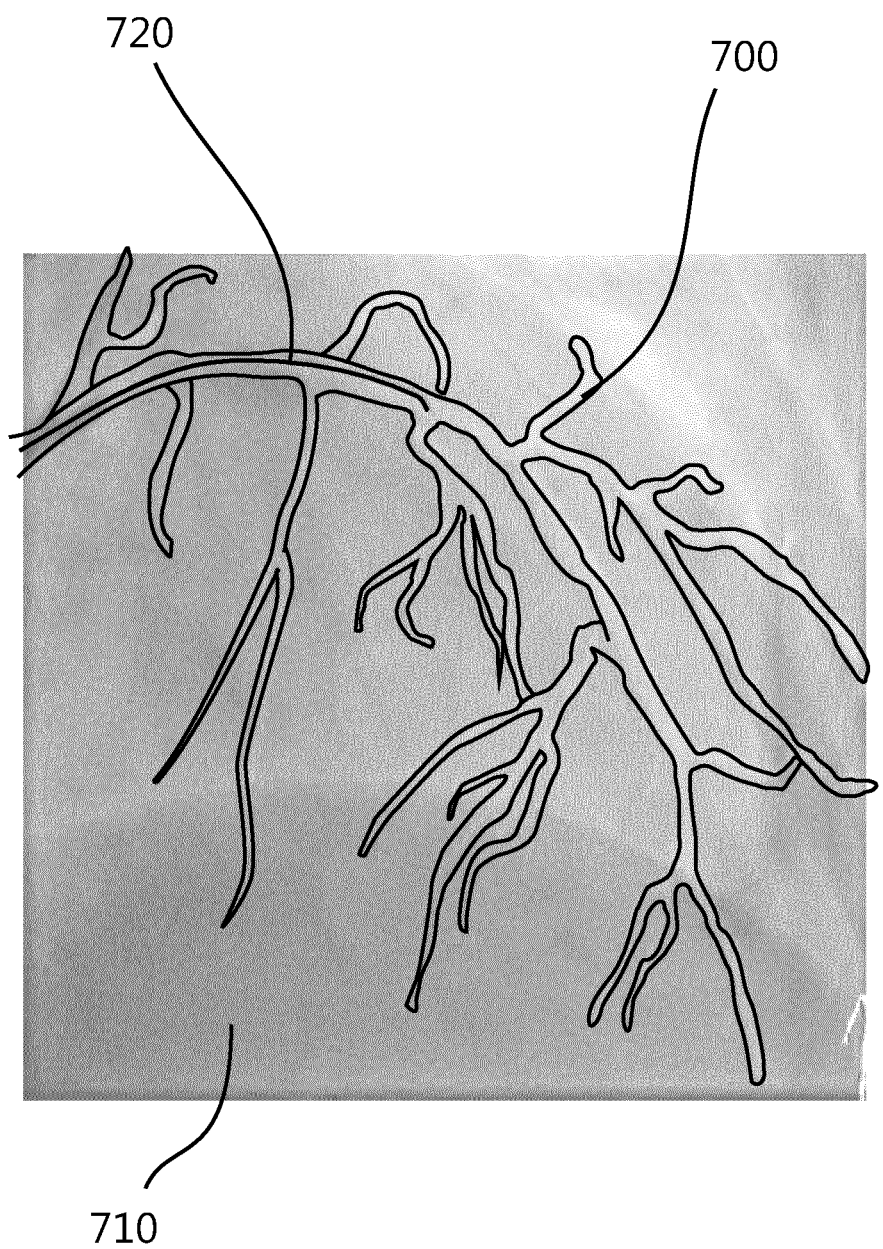
FIG. 7 shows an image provided by the described method.

FIG. 7 shows a typical result obtained with a cardiac roadmapping technique, wherein a previously recorded angiography image 700 is laid over a live fluoroscopy image 710 including a portion of an instrument 720.

In the following, aspects of the above described methods and systems are summarized.

An embodiment of a cardiac navigation application may be equipped with a means to automatically select and activate the "nearest available roadmap".

In an embodiment, the automatic position control may become active automatically, enabling a physician to easily steer the x-ray geometry to an automatically proposed position.

In an embodiment, the newest corresponding roadmap is automatically selected and activated, by sending the x-ray geometry automatically, via a preferred position selection.

In an embodiment, software buttons are added to the user interface of the system, that support switching between roadmaps manually.

In an embodiment, a map of available roadmaps (scatter plot) may show the activated roadmap in color, the actual position of the geometry, and the remaining inactive roadmaps.

In an embodiment, the automatic position control may also be able to steer the patient table automatically to the preferred position.

In an embodiment, the EPX is automatically tuned to the acquisition mode of the corresponding roadmap, i.e. FOV, frame speed, LCA/RCA, which are features that should match as well during overlay.

In an embodiment, the selection criterion for best available roadmap may be different, i.e. not necessarily based on the closest position, but on other properties of the available roadmaps, e.g. a roadmap with the smallest possible foreshortening, given a certain lesion in the vessels.

In an embodiment, roadmapping may be used in combination with Xper Swing acquisition and the selection of the preferred position depends on the optimal view chosen from the Swing acquisition.

Invention can be applied to any X-ray interventional systems used during a PCI intervention. It will be understood that the invention is not restricted to this application area. It could also be used during, for instance, EP guidance and other roadmapping applications. Generally, it can be used for any application in which navigation is the essential element.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the appended claims. In the claims, the word 'comprising' does not exclude other elements or steps, and the indefinite article 'a' or 'an' does not exclude a plurality. A single processor or other unit may fulfill the functions of several items recited in the claims.

The mere fact that certain measures are recited and mutually different dependent claims does not indicate that a combination of these measured cannot be used to advantage. A computer program may be stored/distributed on a suitable medium such as an optical storage medium or a solid-state medium supplied together with or as a part of another hardware, but may also be distributed in other forms, such as via the internet or other wired or wireless telecommunication systems. Any reference signs in the claims should not be construed as limiting the scope.

LIST OF REFERENCE SIGNS 100 database
200 user interface element
210 indication of current imaging parameters
220 indication of selected roadmap
230 indication of nearest roadmap
240 indication of further roadmap
250 button for position control of imaging system
260 button for automatic position control of imaging system
270 button for skip through list of roadmaps
300 monitor
400 x-ray device
410 x-ray source
420 x-ray detector
500 patient table
600 processing device
700 contrast-enhanced image
710 fluoroscopy image
720 portion of an instrument

The invention claimed is:

1. A system for vascular roadmapping comprising:
an imaging device having an x-ray source and an x-ray detector, for generating a fluoroscopy image;
a data base including contrast-enhanced images, wherein the contrast-enhanced images are generated with different imaging parameters;
a user interface configured to select intended imaging parameters; and
a processor configured:
to determine current imaging parameters of the imaging device,
to determine a contrast-enhanced image out of the contrast-enhanced images generated with respective imaging parameters, wherein the contrast-enhanced image has imaging parameters closest to the intended imaging parameters,
to select the contrast-enhanced image to obtain a selected contrast-enhanced image,
to adjust the current imaging parameters of the imaging device to the imaging parameters of the selected contrast-enhanced image, and
to determine that a state of the imaging device is a ready-for-use-state based on a completion of an adjustment of the current imaging parameters of the imaging device from the current imaging parameters to the imaging parameters of the selected contrast-enhanced image,
wherein the imaging parameters of the selected contrast-enhanced image comprises a position of the x-ray source and the x-ray detector, an orientation of the x-ray source and the x-ray detector, settings of the x-ray source, and settings of the x-ray detector, and
wherein the user interface is further configured to indicate the ready-for-use-state or the not-ready-for-use-state of the imaging device.

2. The system of claim 1, further comprising a patient table, wherein the imaging parameters of the selected contrast-enhanced image include a position of the patient table.

3. The system of claim 1, wherein the processor is further configured for generating a roadmap scatterplot including available contrast-enhanced images with respective imaging parameters being close to the intended imaging parameters, and
wherein the selected contrast-enhanced image is selected manually from the roadmap scatterplot.

4. The system of claim 1, wherein the imaging parameters of the selected contrast-enhanced image further include at least one out of the group consisting of frame speed, time and date of generation of a contrast-enhanced image, and smallest foreshortening.

5. The system of claim 1, wherein the processor is further configured to combine the fluoroscopy image with the selected contrast-enhanced image for forming a combined image, and wherein the system further comprises a monitor for displaying the combined image.

6. The system of claim 1, wherein the processor is further configured to identify a cyclic motion in a series of contrast-enhanced images and is configured to identify a cyclic motion in a series of fluoroscopy images, and wherein the processor is further configured to combine a selected fluoroscopy image with a contrast-enhanced image of a corresponding motion cycle.

7. The system of claim 1, wherein the selected contrast-enhanced image is selected automatically based on a deviation of the imaging parameters of the selected contrast-enhanced image from the intended imaging parameters being smallest out of deviations of the imaging parameters of the plurality of contrast-enhanced images, and
wherein the processor is further configured to automatically control the imaging device so as to adjust the current imaging parameters of the imaging device to the imaging parameters of the selected contrast-enhanced image.

8. The system of claim 1, wherein the processor is configured to control the imaging device to:
generate a plurality of fluoroscopy images associated with cardiac cycles based on electro-cardiogram signals;
select a set of the contrast-enhanced images that has the cardiac cycles of the plurality of fluoroscopy images for obtaining a set of selected contrast-enhanced images;
adjust the current imaging parameters of the imaging device to the imaging parameters of the set of selected contrast-enhanced images to form adjusted fluoroscopy images; and
combine the adjusted fluoroscopy images with the selected set of the contrast-enhanced images.

9. The system of claim 1, wherein the processor is configured to control the imaging device to:
generate a plurality of fluoroscopy images to determine cyclic motion in the plurality of fluoroscopy images based on image analysis of the plurality of fluoroscopy images;
select a set of the contrast-enhanced images that has the cyclic motion of the plurality of fluoroscopy images for obtaining a set of selected contrast-enhanced images;

adjust the current imaging parameters of the imaging device to the imaging parameters of the set of selected contrast-enhanced images to form adjusted fluoroscopy images; and combine the adjusted fluoroscopy images with the selected set of the contrast-enhanced images.

10. A method for vascular roadmapping, the method comprising the acts of:

receiving intended imaging parameters for a fluoroscopy image to be obtained by an imaging device having an x-ray source and an x-ray detector;

determining a contrast-enhanced image out of a plurality of contrast-enhanced images generated with respective imaging parameters, wherein the contrast-enhanced image has imaging parameters closest to the intended imaging parameters;

selecting the contrast-enhanced image to obtain a selected contrast-enhanced image;

adjusting current imaging parameters of the imaging device from the current imaging parameters to the imaging parameters of the selected contrast-enhanced image; and providing a ready-for-use-state of the imaging device when the adjusting act is completed, wherein the imaging parameters of the selected contrast-enhanced image comprises a position of the x-ray source and the x-ray detector, an orientation of the x-ray source and the x-ray detector, settings of the x-ray source, and settings of the x-ray detector.

11. The method of claim 10, further comprising the acts of generating a fluoroscopy image with the imaging parameters of the selected contrast-enhanced image, the fluoroscopy image including an instrument in an anatomy part;

receiving from a data base the selected contrast-enhanced image with the imaging parameters of the selected contrast-enhanced image; and combining the fluoroscopy image with the selected contrast-enhanced image.

12. The method of claim 11, wherein the combining act forms a combined image, and the method further comprising the act of displaying the combined image.

13. The method of claim 10, further comprising the act of providing a roadmap scatterplot including available contrast-enhanced images with imaging parameters being close to the intended imaging parameters.

14. A non-transitory computer readable medium comprising computer instructions which, when executed by a processor, configure the processor to perform a method for vascular roadmapping, the method comprising the acts of:

receiving intended imaging parameters for a fluoroscopy image to be obtained by an imaging device having an x-ray source and an x-ray detector;

determining a contrast-enhanced image out of a plurality of contrast-enhanced images generated with respective imaging parameters, wherein the contrast-enhanced image has imaging parameters closest to the intended imaging parameters;

selecting the contrast-enhanced image to obtain a selected contrast-enhanced image;

adjusting current imaging parameters of the imaging device from the current imaging parameters to the imaging parameters of the selected contrast-enhanced image; and providing a ready-for-use-state of the imaging device when the adjusting act is completed, wherein the imaging parameters of the selected contrast-enhanced image comprises a position of the x-ray source and the x-ray detector, an orientation of the x-ray source and the x-ray detector, settings of the x-ray source, and settings of the x-ray detector.

* * * * *